US006379325B1

(12) United States Patent
Benett et al.

(10) Patent No.: US 6,379,325 B1
(45) Date of Patent: Apr. 30, 2002

(54) OPTO-ACOUSTIC TRANSDUCER FOR MEDICAL APPLICATIONS

(75) Inventors: William Benett, Livermore; Peter Celliers, Berkeley; Luiz Da Silva, Danville; Michael Glinsky, Livermore; Richard London, Orinda; Duncan Maitland, Livermore; Dennis Matthews, Moss Beach; Peter Krulevich, Pleasanton; Abraham Lee, Walnut Creek, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/350,494

(22) Filed: Jul. 9, 1999

Related U.S. Application Data

(62) Division of application No. 08/639,018, filed on Apr. 24, 1996, now Pat. No. 5,944,687.

(51) Int. Cl.[7] ......................... A61B 17/20; A61B 18/18
(52) U.S. Cl. .......................................... 604/22; 606/15
(58) Field of Search ............................... 604/20, 21, 22; 606/15, 7, 2.5, 10, 2, 3, 13–16, 127, 128

(56) References Cited

U.S. PATENT DOCUMENTS

| 3,532,181 A | 10/1970 | DeMaria et al. |
| 4,334,321 A | 6/1982 | Edelman |
| 4,503,564 A | 3/1985 | Edelman et al. |
| 4,538,609 A | 9/1985 | Takenaka et al. |

(List continued on next page.)

FOREIGN PATENT DOCUMENTS

| AT | 0308634 | 11/1985 |
| DE | 3038445 | 5/1982 |
| DE | 3812841 | 2/1989 |
| EP | 0571306 | 11/1993 |
| WO | WO 9001300 | 2/1990 |

(List continued on next page.)

OTHER PUBLICATIONS

Linde et al., "Shock Waves in Solids," *Scientific America*, May 1969, pp. 83–91.
Bhatta et al., "Effects of Shielded or Unshielded Laser and Electrohydraulic Lithotripsy on Rabbit Bladder," *The Journal of Urology*, vol. 143, No. 4, pp. 857–860, Apr. 1990.
Davros et al., "Gallstone Lithotripsy: Relevant Physical Principles and Technical Issues[1]," The Department of Radiology, Brown University Medical Center, 7 pages (1991).
Van Leeuwen et al., "Noncontact Tissue Ablation by Holmium: YSGG Laser Pulses in Blood," *Lasers in Surgery and Medicine* 11:26–34 (1991).

*Primary Examiner*—Sharon Kennedy
(74) *Attorney, Agent, or Firm*—John P. Wooldridge; Alan H. Thompson

(57) ABSTRACT

This invention is an optically activated transducer for generating acoustic vibrations in a biological medium. The transducer is located at the end of a fiber optic which may be located within a catheter. Energy for operating the transducer is provided optically by laser light transmitted through the fiber optic to the transducer. Pulsed laser light is absorbed in the working fluid of the transducer to generate a thermal pressure and consequent adiabatic expansion of the transducer head such that it does work against the ambient medium. The transducer returns to its original state by a process of thermal cooling. The motion of the transducer within the ambient medium couples acoustic energy into the medium. By pulsing the laser at a high repetition rate (which may vary from CW to 100 kHz) an ultrasonic radiation field can be established locally in the medium. This method of producing ultrasonic vibrations can be used in vivo for the treatment of stroke-related conditions in humans, particularly for dissolving thrombus. The catheter may also incorporate anti-thrombolytic drug treatments as an adjunct therapy and it may be operated in conjunction with ultrasonic detection equipment for imaging and feedback control.

10 Claims, 4 Drawing Sheets

U.S. PATENT DOCUMENTS

| | | | |
|---|---|---|---|
| 4,576,177 A | 3/1986 | Webster, Jr. |
| 4,589,415 A | 5/1986 | Haaga |
| 4,770,653 A | 9/1988 | Shturman |
| 4,775,361 A | 10/1988 | Jacques et al. |
| 4,813,930 A | 3/1989 | Elliott |
| 4,832,024 A | 5/1989 | Boussignac et al. |
| 4,834,093 A | 5/1989 | Littleford et al. |
| 4,844,585 A | 7/1989 | Culshaw et al. |
| 4,852,567 A | 8/1989 | Sinofsky |
| 4,862,886 A | 9/1989 | Clarke et al. |
| 4,887,605 A | 12/1989 | Angelsen et al. |
| 4,900,921 A | 2/1990 | Spillman |
| 4,913,142 A | 4/1990 | Kittrell et al. |
| 4,927,427 A | 5/1990 | Kriauciunas et al. |
| 4,932,954 A | 6/1990 | Wondrazek et al. |
| 4,985,028 A | 1/1991 | Isner et al. |
| 5,005,180 A | 4/1991 | Edelman et al. |
| 5,010,886 A | 4/1991 | Passafaro et al. |
| 5,026,366 A | 6/1991 | Leckrone |
| 5,026,367 A | 6/1991 | Leckrone et al. |
| 5,029,588 A | 7/1991 | Yock et al. |
| 5,041,108 A | 8/1991 | Fox et al. |
| 5,041,121 A | 8/1991 | Wondrazek et al. |
| 5,058,570 A | 10/1991 | Idemoto et al. |
| 5,059,200 A | 10/1991 | Tulip |
| 5,069,664 A | 12/1991 | Guess et al. |
| 5,109,859 A | 5/1992 | Jenkins |
| 5,116,227 A | 5/1992 | Levy |
| 5,146,917 A | 9/1992 | Wagnières et al. |
| 5,152,768 A | 10/1992 | Bhatta |
| 5,158,560 A | 10/1992 | Sogawa et al. |
| 5,163,421 A | 11/1992 | Bernstein et al. |
| 5,188,632 A | 2/1993 | Goldenberg |
| 5,193,526 A | 3/1993 | Daikuzono |
| 5,217,454 A | 6/1993 | Khoury |
| 5,219,401 A | 6/1993 | Cathignol et al. |
| 5,224,942 A | 7/1993 | Beuchat et al. |
| 5,254,112 A | 10/1993 | Sinofsky et al. |
| 5,254,114 A | 10/1993 | Reed, Jr. et al. |
| 5,300,066 A | 4/1994 | Manoukian et al. |
| 5,304,115 A | 4/1994 | Pflueger et al. |
| 5,304,171 A | 4/1994 | Gregory et al. |
| 5,324,255 A | 6/1994 | Passafaro et al. |
| 5,324,282 A | 6/1994 | Dodick |
| 5,326,342 A | 7/1994 | Pflueger et al. |
| 5,334,207 A | 8/1994 | Gay, Jr. |
| 5,342,355 A | 8/1994 | Long |
| 5,350,375 A | 9/1994 | Deckelbaum et al. |
| 5,350,377 A | 9/1994 | Winston et al. |
| 5,353,262 A | 10/1994 | Yakymyshyn et al. |
| 5,354,324 A | 10/1994 | Gregory |
| 5,366,490 A | 11/1994 | Edwards et al. |
| 5,368,558 A | 11/1994 | Nita |
| 5,370,609 A | 12/1994 | Drasler et al. |
| 5,377,683 A | 1/1995 | Barken |
| 5,380,273 A | 1/1995 | Dubrul et al. |
| 5,397,293 A | 3/1995 | Alliger et al. |
| 5,397,301 A | 3/1995 | Pflueger et al. |
| 5,399,158 A | 3/1995 | Lauer et al. |
| 5,472,406 A | 12/1995 | de la Torre et al. |
| 5,474,530 A | 12/1995 | Passafaro et al. |
| 5,486,170 A | 1/1996 | Winston et al. |
| 5,662,590 A | 9/1997 | de la Torre et al. |
| 5,944,687 A * | 8/1999 | Benett et al. ............... 604/22 |
| 5,957,914 A * | 9/1999 | Cook et al. .................. 606/6 |

FOREIGN PATENT DOCUMENTS

| | | |
|---|---|---|
| WO | WO 9009762 | 9/1990 |
| WO | 9012544 | 11/1990 |
| WO | 9110403 | 7/1991 |
| WO | 9111963 | 8/1991 |
| WO | 9206739 | 4/1992 |
| WO | 9216739 | 4/1992 |
| WO | WO 9314689 | 8/1993 |
| WO | WO 9311711 | 9/1993 |
| WO | WO 9408523 | 4/1994 |

\* cited by examiner

OPTO-ACOUSTIC TRANSDUCER FOR MEDICAL APPLICATIONS

This application is a Division of Ser. No. 08/639,018 filed Apr. 24, 1996, now U.S. Pat. No. 5,944,687.

The United States Government has rights in this invention pursuant to Contract No. W-7405-ENG48 between the United States Department of Energy and the University of California for the operation of Lawrence Livermore National Laboratory.

BACKGROUND OF THE INVENTION

1. Field of the Invention

The present invention relates to the removal of blockages in tubular tissues and organs, and more specifically, it relates to the use of a light stimulated opto-acoustic transducer located at the end of a fiber optic within a catheter for use in ultrasound thrombolysis and angioplasty.

2. Description of Related Art

Ischemic strokes are caused by the formation or lodging of thrombus in the arterial network supplying the brain. Typically these occlusions are found in the carotid artery or even smaller vessels located still higher in the cranial cavity. Interventional cardiologists and vascular surgeons have devised minimally invasive procedures for treating these conditions in the vasculature elsewhere in the body. Among these treatments is ultrasound angioplasty whereby a microcatheter is directed to the site of an occlusion. An ultrasonic transducer is coupled to a transmission medium that passes within the catheter and transmits vibrations to a working tip at the distal end in dose proximity to the occlusion. Ultrasonic catheters for dissolving atherosclerotic plaque and for facilitating clot lysis have been described previously. Improvements on these inventions have concentrated on improving the operation or function of the same basic device (Pflueger et al., U.S. Pat. No. 5,397,301). The vibrations coupled into the tissues help to dissolve or emulsify the clot through various ultrasonic mechanisms such as cavitation bubbles and microjets which expose the clot to strong localized shear and tensile stresses. These prior art devices are usually operated in conjunction with a thrombolytic drug and/or a radiographic contrast agent to facilitate visualization.

The ultrasonic catheter devices all have a common configuration in which the source of the vibrations (the transducer) is external to the catheter. The vibrational energy is coupled into the proximal end of the catheter and transmitted down the length of the catheter through a wire that can transmit the sound waves. There are associated disadvantages with this configuration: loss of energy through bends and curves with concomitant heating of the tissues in proximity; the devices are not small enough to be used for treatment of stroke and are difficult to scale to smaller sizes; it is difficult to assess or control dosimetry because of the unknown and varying coupling efficiency between the ultrasound generator and the distal end of the catheter. Dubrul et al., U.S. Pat. No. 5,380,273, attempts to improve on the prior art devices by incorporating advanced materials into the transmission member. Placement of the ultrasonic transducer itself at the distal end of the catheter has been impractical for a number of reasons including size constraints and power requirements.

A related method for removing occlusions is laser angioplasty in which laser light is directed down an optical fiber to impinge directly on the occluding material. Laser angioplasty devices have been found to cause damage to or destruction of the surrounding tissues. In some cases uncontrolled heating has lead to vessel perforation. The use of high energy laser pulses at a low or moderate repetition rate, e.g. around 1 Hz to 100 Hz, results in non-discriminatory stress waves that significantly damage healthy tissue and/or result in insufficient target-tissue removal when the independent laser parameters are adjusted such that healthy tissue is not affected. Use of high energy laser light to avoid thermal heating has been found to cause damage through other mechanisms that puncture or otherwise adversely affect the tissue.

SUMMARY OF THE INVENTION

It is an object of the present invention to provide an opto-acoustic transducer located at the end of a fiber optic within a catheter for use in the removal of either partial or complete vascular blockage, or other luminal occlusions.

The invention has uses in therapeutic applications of angioplasty and thrombolysis. Angioplasty is the removal of atherosclerotic plaque and thrombolysis is the removal of soft clots which are typical in the brain and in the coronary arteries. The problems of energy transmission through the catheter are addressed by using an optical fiber to guide laser pulses to the distal end. Unlike laser angioplasty or laser thrombolysis, direct ablation of the occlusion is not attempted; rather, a high frequency train of small laser pulses is used as an energy source for a miniature ultrasonic transducer. This transducer can be used in a similar fashion to the prior art catheter-based ultrasonic devices. Dissolution of the occlusion is then promoted by the ultrasonic action, and not directly by the interaction with the laser light.

The use of optical energy to induce an ultrasonic excitation in the transducer offers a number of advantages. Most importantly, it can be implemented through a 2.5 French or smaller catheter, such as is required for accessing dots in the cerebrovasculature. Optical fibers can be fabricated to small dimensions, yet are highly transparent and capable of delivering substantial optical power densities from the source to the delivery site with little or no attenuation. The opto-acoustic transducer provides for variable energy delivery by means of independent control over light delivery/working fluid coupling. The working fluid is a substance contained within the transducer which absorbs the optical energy. Engineering design parameters include optical wavelength, optical energy, light pulse duration, light pulse repetition frequency, light pulse duty cycle, fiber dimensions, fiber materials, scattering and absorption of the optical energy in the working fluid, and the thermodynamic parameters of the working fluid. The additional engineering of the mechanical transducer head results in acoustic energy of appropriate magnitude and frequency such that targeted occlusions are preferentially damaged while healthy tissues remain intact or otherwise minimally affected. The present invention will allow delivery of sufficient energy to generate acoustic excitation through a small and flexible catheter, such as is required for stroke treatment.

DETAILED DESCRIPTION OF THE INVENTION

Figure 1:
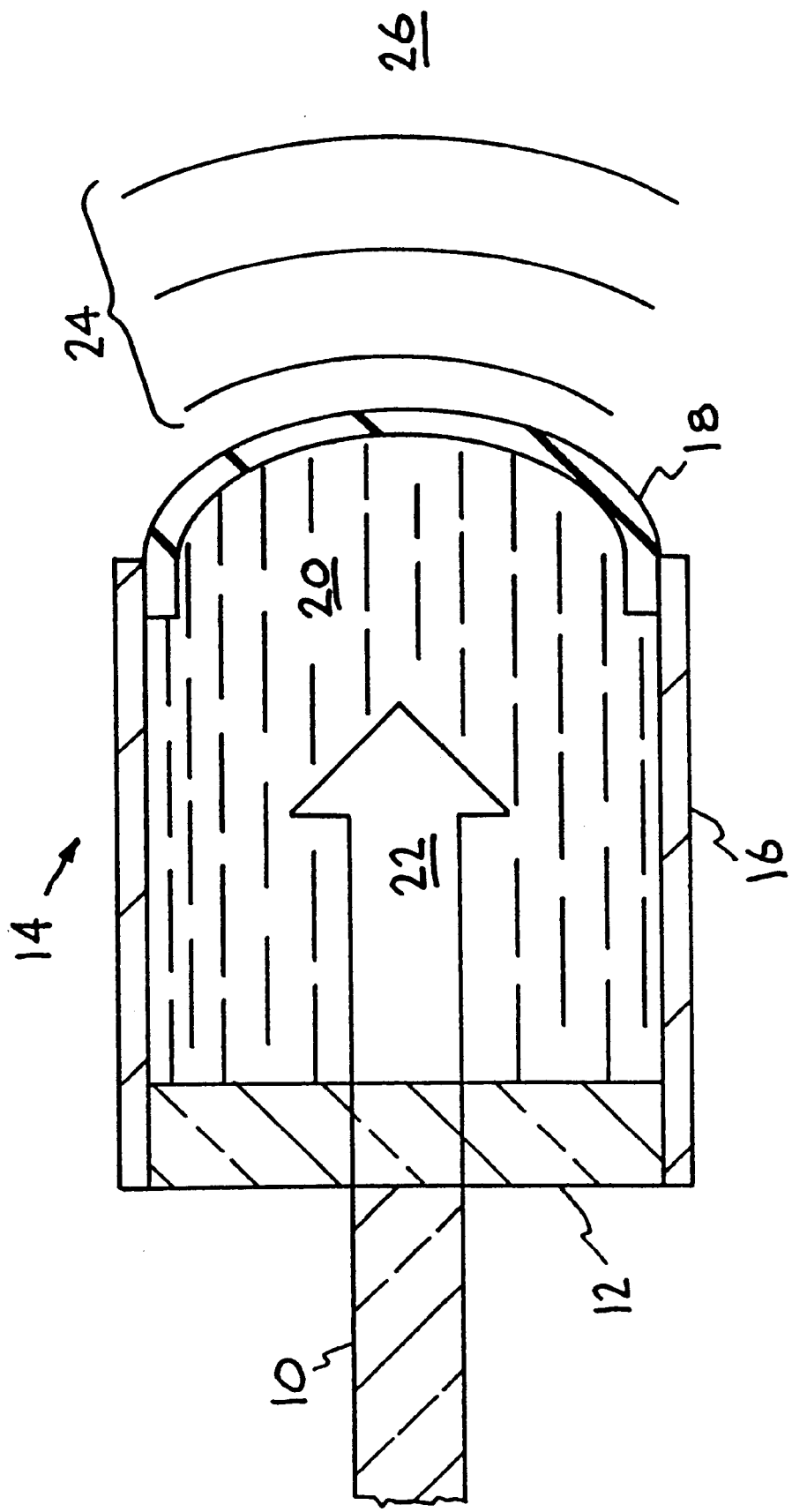
FIG. 1 shows an embodiment of the opto-acoustic transducer of the present invention.

The invention is a laser light stimulated opto-acoustic transducer operatively located at the end of a fiber optic, for use in ultrasound thrombolysis and angioplasty. The fiber optic may be located within a catheter. The transducer converts pulsed optical energy to acoustic energy in a liquid ambient medium. The pulsed optical energy is most conveniently provided by a laser source operating at the desired repetition rate. The laser wavelength can be chosen to operate anywhere from 200 nm to 5000 nm such that the wavelength can be transmitted efficiently through the fiber optic. Pulse energy density may vary from 0.01 J/cm$^2$ to 4 J/cm$^2$, pulse duration from 3 ns to 1 $\mu$s, and pulse frequency, or repetition rate may vary from 10 Hz to 100 kHz. Referring to FIG. 1, the opto-acoustic transducer comprises a fiber optic 10 (plastic or glass) which terminates at an optional transparent window 12 of the transducer 14, which consists of a rigid container 16, a flexible membrane 18 and a working fluid 20. In some embodiments, the fiber itself can act as the transparent window, such that the container is formed around the fiber tip. The cylinder may comprise a high thermal conductivity, e.g., greater than 200 W/m-K, such as can be fabricated with metal alloys or with diamond (2000 W/m-K).

FIG. 1 shows the delivery of pulsed optical energy 22 from fiber optic 10 through the transparent window 12 into the working fluid 20 to produce acoustic waves 24 in an ambient medium 26. The range of the acoustic waves can be from continuous wave (CW) to 100 kHz. The transparent window 12, rigid container 16 and flexible membrane 18 together define a confined volume. Flexible membrane 18 will allow expansions and contractions of the working fluid within the confined volume to be transmitted to an external medium (such as the ambient medium 26). Transparent window 12 may comprise glass, sapphire, diamond or quartz, and may be used for the protection of plastic fibers from acoustic damage. The transparent window allows transmission of pulsed optical energy to be absorbed by the working fluid 20 contained within the structure. The window can be attached to the fiber tip with a suitable optical cement or epoxy adhesive. An additional element (not shown in FIG. 1), consisting of a rigid structure possessing an open structure (holes or channels) or a porous structure may be placed in the volume to facilitate absorption of the laser energy and shorten the thermal relaxation time constant of the system while providing space for containing the working fluid.

Figure 2:
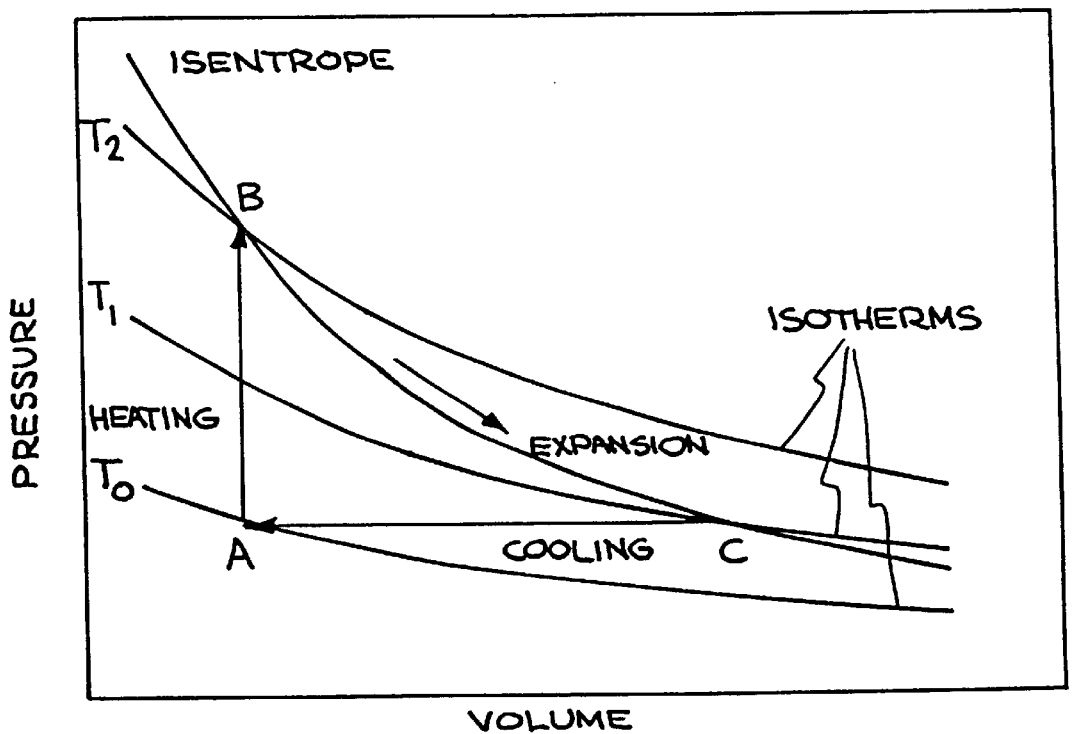
FIG. 2 shows a possible thermodynamic cycle of the opto-acoustic transducer.

The opto-acoustic transducer of the present invention operates on thermodynamic principles similar to those describing the thermodynamics of a heat engine. FIG. 2 is a diagram of a possible thermodynamic path of the working fluid contained within the transducer volume. For the purposes of explanation, the transducer operation is described based on this particular example, although other thermodynamic cycles may be possible depending on the parameters of the particular device. The thermodynamic path maps out a cycle on the PV plane, where P is the fluid pressure, and V is the fluid specific volume. In this example, the inertial response time of the transducer coupled to the ambient medium is assumed to be long compared to the laser pulse duration, and short compared to the thermal relaxation time of the device. The cycle begins at point A on the diagram where the working fluid is in equilibrium with the ambient pressure and temperature. When a short pulse of optical energy is absorbed in the working fluid, the internal energy is increased and the fluid is heated (A to B). As a consequence of this heating, the fluid temperature is raised, and also the fluid pressure. The force of the fluid pressure against the membrane causes expansion of the fluid (B to C) and motion of the transducer membrane into the ambient fluid. This process takes place adiabatically on a time scale shorter than the thermal relaxation time of the transducer within the ambient medium. In the third phase of the cycle, the heated fluid relaxes to the temperature of the ambient medium as the energy deposited in the transducer is carried off by thermal conduction to the ambient medium (C to A). The net mechanical work done on the ambient fluid during this cycle is represented by the area contained in the triangle bounded by the process cycle. This idealized cycle does not take into account irreversible loss mechanisms.

Figure 3:
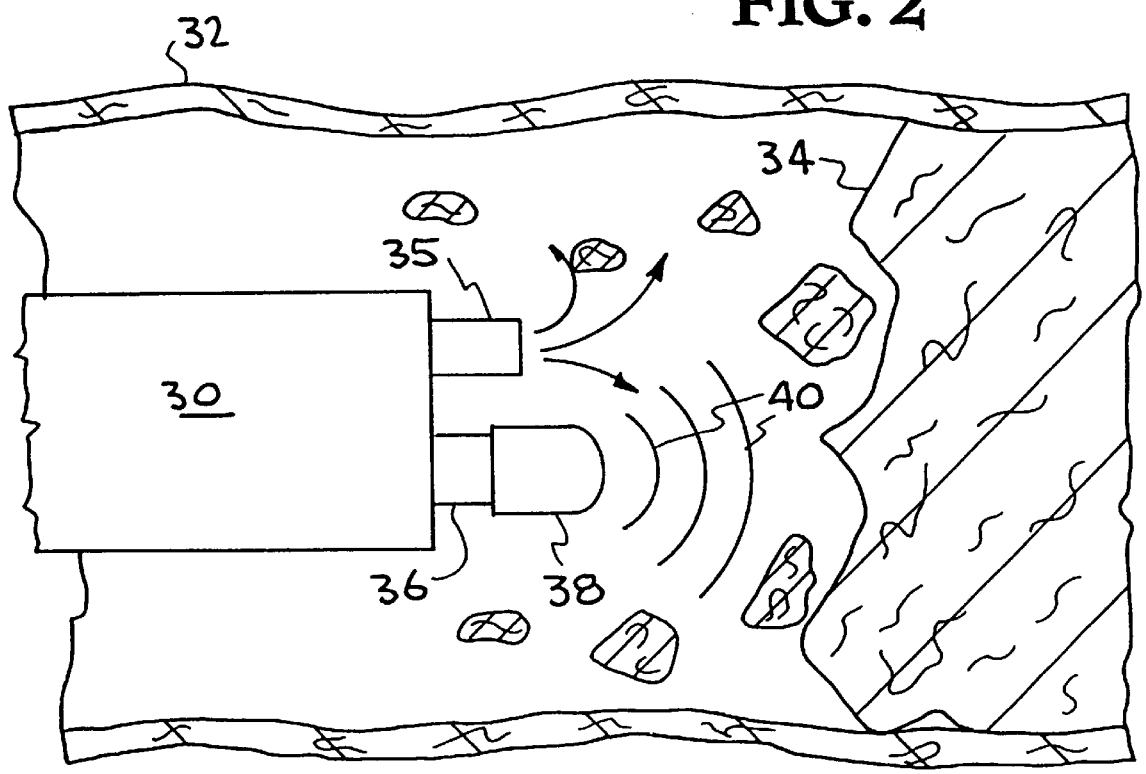
FIG. 3 shows an embodiment of the opto-acoustic transducer in an endovascular catheter.

FIG. 3 shows an embodiment of the opto-acoustic transducer in an endovascular catheter. Catheter 30 is located within a blood vessel 32 near an occlusion 34. An adjunct fluid delivery tube 35 and an optical fiber 36 with an opto-acoustic transducer 38 are located within catheter 30. The figure depicts the generation of ultrasonic vibration waves 40 by opto-acoustic transducer 38 to break up the occlusion 34. As an aid to the process, an adjunct fluid 42 is delivered to the occlusion 34. The adjunct fluid is a thrombolytic fluid or agent.

A particular embodiment of the present invention comprises, for example, a 400 $\mu$m diameter optical fiber, a titanium cylinder of appropriate size attached to the end of the fiber, a working fluid filling the cylinder cavity, and an elastic membrane attached to the end of the cylinder opposite the fiber to form a seal. The elastic membrane is filled with the working fluid, then placed over the fiber tip and attached. The working fluid contained in the transducer can be dyed water, saline or an inert fluid with low critical temperature, such as a chloro-fluorocarbon fluid (e.g. $C_6F_{12}$) with critical point temperatures in the range of 250 K to 450 K. The optical fiber is coupled at the proximal end to a high repetition rate laser system which injects pulses of light into the fiber. The light emerging from the fiber at the distal end is absorbed by the working fluid contained in the transducer. The optical fiber functions primarily as a means of energy transmission such that the optical energy produced by the laser is delivered to the transducer with little or no loss.

Figure 4:
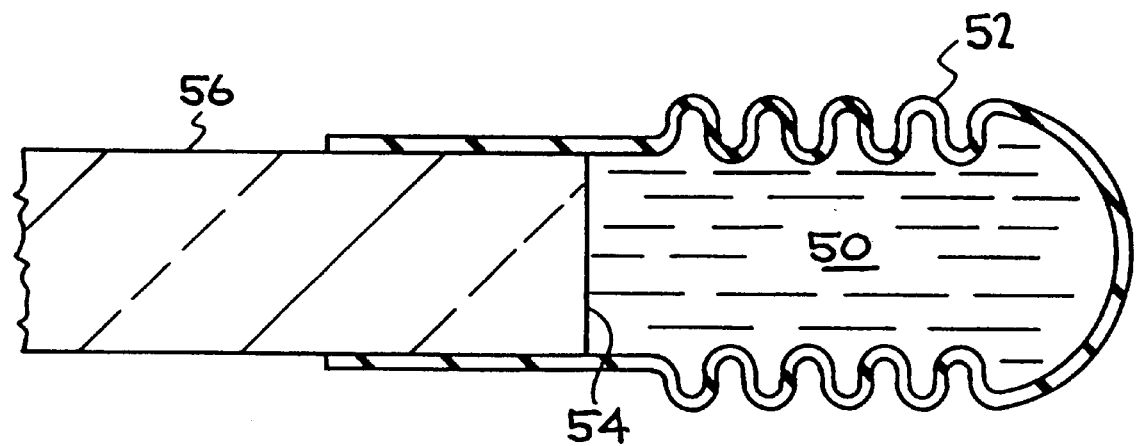
FIG. 4 shows an embodiment of the invention using a bellows head.

A bellows-type opto-acoustic transducer head, shown in FIG. 4 has a light-absorbing fluid 50 contained within a bellows head 52, and the transducer is attached over the tip 54 of fiber optic 56. Light from the laser source is absorbed by the entrapped fluid 50, the fluid vaporizes causing a pressure rise, and the bellows expands axially, impinging on the clot or plaque. In one embodiment, dimensions of the invention in inches include (i) a fiber diameter of 0.041, (ii) a bellows assembly length of 0.252, (iii) a bellows tip of 0.103, (iv) a bellows diameter of 0.061 and (v) a bellows wall thickness of 0.002. The advantages of this type of device include: directed motion of the pressure wave, it does not use blood for energy absorption, and the transducer may be excited in a resonant mode, increasing the amount of axial motion. In the resonant mode, when the pulses of laser energy are transmitted at the proper frequency (resonant frequency) the amplitude of motion of the transducer head will be significantly larger than at other frequencies. Alternatively, at this frequency significantly less laser energy will be needed to achieve a given displacement. The resonant frequency can be adjusted by varying the stiffness of the transducer. The bellows transducer 52 is made by precision machining a mandrel such that it has the desired internal dimensions of the transducer. The transducer head can be made of any bio-compatible metal which can be electroplated or electrodeless plated, such as platinum or gold. Non-bio-compatible metals such as copper or nickel may be used if they are coated with a bio-compatible layer. The metal is plated over the mandrel to the desired thickness, e.g. 10 $\mu$m–100 $\mu$m, and the mandrel is selectively dissolved away using a wet chemical etchant, leaving the hollow transducer.

Figure 5:
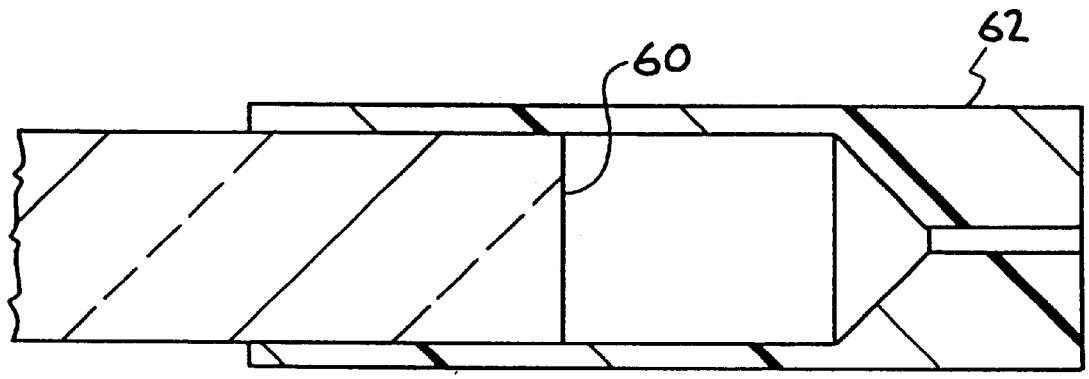
FIG. 5 shows an embodiment of the invention using a nozzle.

Nozzles for placement at the fiber tip 60 have also been fabricated, as shown in FIG. 5. This will serve to increase the velocity of the fluid flow (e.g., blood) away from the catheter tip, and to direct the fluid flow in the axial direction. Also, the fluid flow could be directed obliquely, including perpendicular, to the fiber axis with one or more holes through the side of the nozzle 62. The nozzle can use blood or perfused saline as the working fluid. Adjunct therapy also can be used with the nozzle. Nozzles are fabricated using conventional machining of metals or plastics, injection molding, and electroforming (bellows process).

Figure 6:
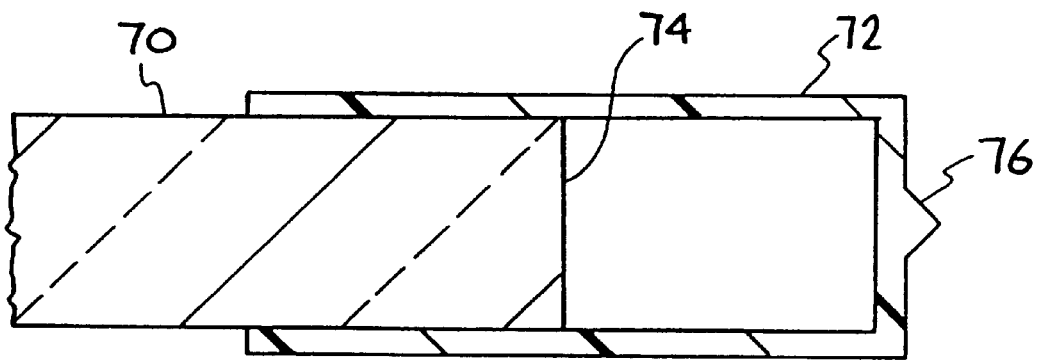
FIG. 6 shows an embodiment of the invention using a cantilever-type device.

FIG. 6 shows a spring-type device. A fiber optic 70 with a rigid container 72 located at its distal end 74 has a suspended tip 76 which covers the open end of rigid container 72. The tip 76 is not attached all the way around the open end of rigid container 72; rather, it is attached by a suspension which allows it to deflect outwards from the end of container 72. The tip may be formed of silicon, may be flat or, as shown in the Figure, may have a shape formed thereon to increase the ability of the device to exert force on a blockage. When inserted into a blood sample or blood filled vasculature, blood seeps through the unconnected portion of the suspended tip or cantilever, and fills the volume defined by the rigid container 72, the distal end 74 of the fiber 70 and the cantilever or suspended tip 76. Upon operation, a laser pulse initiates a thermodynamic cycle in the blood within the confined volume which actuates the tip 76. Alternatively, saline or other fluid can be continuously introduced into the cavity for use as the working fluid.

Figure 7:
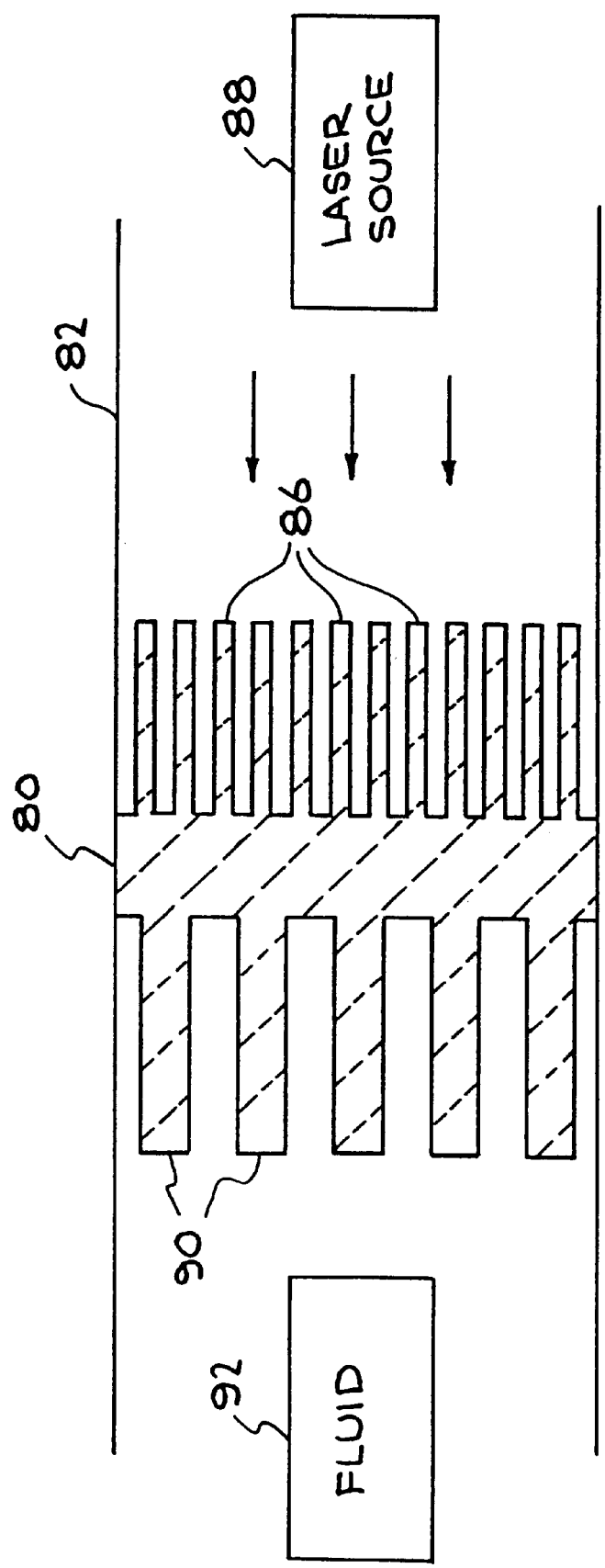
FIG. 7 shows an embodiment of the invention using a microchannel device for converting optical to thermal energy.

FIG. 7 shows a microchannel device. This device comprises a microchannel element 80 located at the distal end of fiber optic 82. The side 86 of microchannel element 80 that is facing the laser radiation source (shown as block 88) comprises fine pitched microchannels or another laser radiation trapping or absorbing surface. The side 90 of microchannel element 80 that is facing the fluid (shown as block 92) comprises a microchannel structure to increase the surface area and to enhance the thermal transfer from the laser radiation source 88 to the fluid 92. The microchannels are fabricated by anisotropically etching a {110}-oriented single crystal of silicon using silicon nitride as a masking layer. Standard photolithographic techniques are used to pattern the silicon nitride, and the silicon is etched using a solution of potassium hydroxide in water. As an alternative to microchannels, a porous silicon structure can be used. Porous silicon is fabricated using an electrochemical hydrofluoric acid etch of a single crystal of silicon.

Applications envisioned for this invention include any method or procedure whereby localized ultrasonic excitations are to be produced in the body using a catheter system for guidance and delivery. The invention may be used in (i) endovascular treatment of vascular occlusions that lead to ischemic stroke (This technology can lyse thrombus and lead to reperfusion of the affected cerebral tissue), (ii) endovascular treatment of cerebral vasospasm (This technology can relax vaso-constriction leading to restoration of normal perfusion and therefore prevent further transient ischemic attacks or other abnormal perfusion situations), (iii) endovascular treatment of cardiovascular occlusions (This technology can lyse thrombus or remove atherosclerotic plaque from arteries), (iv) endovascular treatment of stenoses of the carotid arteries, (v) endovascular treatment of stenoses of peripheral arteries, (vi) general restoration of patency in any of the body's luminal passageways wherein access can be facilitated via percutaneous insertion, (vii) any ultrasonic imaging application where a localized (point) source of ultrasonic excitation is needed within an organ or tissue location accessible through insertion of a catheter, (viii) lithotriptic applications including therapeutic removal of gallstones, kidney stones or other calcified objects in the body and (ix) as a source of ultrasound in ultrasound modulated optical tomography.

The pulsed laser energy source used by this invention can be based on a gaseous, liquid or solid state medium. Rare earth-doped solid state lasers, ruby lasers, alexandrite lasers, Nd:YAG lasers and Ho:YLF lasers are all examples of lasers that can be operated in a pulsed mode at high repetition rate and used in the present invention. Any of these solid state lasers may incorporate non-linear frequency-doubling or frequency-tripling crystals to produce harmonics of the fundamental lasing wavelength. A solid state laser producing a coherent beam of visible or ultraviolet radiation may be employed directly with the invention or used in conjunction with a dye laser to produce an output beam which is tunable over a wide portion of the ultraviolet and visible spectrum. Tunability over a wide spectrum provides a broad range of flexibility for matching the laser wavelength to the absorption characteristics of the working fluid contained in the transducer. The output beam is coupled by an optical fiber to the acousto-optic transducer at the surgical site through, for example, a percutaneous catheter. In operation, a pulsed beam of light actuates the transducer which removes and/or emulsifies thrombus or atherosclerotic plaque with less damage to the underlying tissue and less chance of perforating the blood vessel wall than prior art devices.

Various other pulsed lasers can be substituted for the disclosed laser sources. Similarly, various dye materials can be used in the dye laser. Configurations other than a free-flowing dye, such as dye-impregnated plastic films or cuvette-encased dyes, can be substituted in the dye laser. The dye laser can also store a plurality of different dyes and substitute one for another automatically in response to user-initiated control signals or conditions encountered during use (e.g. when switching from a bloodfilled field to a saline field or in response to calcific deposits). Suitable dyes for use in the dye laser components of the invention include, for example, P-terphenyl (peak wavelength 339); BiBuQ (peak wavelength: 385); DPS (peak wavelength: 405); and Coumarin 2 (peak wavelength: 448).

In yet another embodiment the pulsed light source may be an optical parametric oscillator (OPO) pumped by another solid-state laser. OPO systems allow for a wide range of wavelength tunability in a compact system comprised entirely of solid state optical elements. The laser wavelength in OPO systems may also be varied automatically in response to user-initiated control signals or conditions encountered during use.

Catheters, useful in practicing the present invention, can take various forms. For example, one embodiment can consist of a catheter having an outer diameter of 3.5 millimeters or less, preferably 2.5 millimeters or less. Disposed within the catheter is the optical fiber which can be a 400 micron diameter or smaller silica (fused quartz) fiber such as the model SG 800 fiber manufactured by Spectran, Inc. of Sturbridge, Mass. The catheter may be multi-lumen to provide flushing and suction ports. In one embodiment the catheter tip can be constructed of radio-opaque and heat resistant material. The radio-paque tip can be used to locate the catheter under fluoroscopy.

The invention can be used with various catheter devices, including devices which operate under fluoroscopic guidance as well as devices which incorporate imaging systems, such as echographic or photoacoustic imaging systems or optical viewing systems. For one example of a photoacoustic imaging system which can be specifically adapted for the catheter environment, see U.S. Pat. No. 4,504,727 incorporated herein by reference.

Changes and modifications in the specifically described embodiments can be carried out without departing from the scope of the invention, which is intended to be limited by the scope of the appended claims.

What is claimed is:

1. A method for removing a vascular occlusin, comprising:

inserting a catheter into a blood vessel, wherein said catheter comprises:
  a fiber optic having a proximal end and a distal end; and
  an opto-acoustic transducer fixedly and operatively connected to said distal end of said fiber optic, wherein said opto-acoustic transducer comprises a working fluid, wherein said opto-acoustic transducer vibrates when stimulated by light propagated through said fiber optic; and said method further comprising coupling a high repetition rate laser beam into said fiber, wherein said beam is absorbed by said working fluid, wherein said transducer generates acoustic waves to remove a vascular occlusion within said blood vessel.

2. The method of claim 1, wherein said high repetition rate laser beam has a pulse frequency within the range of 10 Hz to 100 kHz.

3. The method of claim 1, wherein said high repetition rate laser beam has a wavelength within the range of 200 nm to 5000 nm.

4. The method of claim 1, wherein said high repetition rate laser beam has a pulse energy density within the range of 0.01 J/cm$^2$ to 4 J/cm$^2$.

5. The method of claim 1, wherein said high repetition rate laser beam has a pulse duration of less than 200 ns.

6. The method of claim 1, wherein said high repetition rate laser beam has a pulse duration that is sinusoidal.

7. The method of claim 1, wherein said high repetition rate laser beam has a pulse duration that is less than 1 $\mu$s.

8. The method of claim 1, wherein said high repetition rate laser beam has (i) a pulse frequency within the range of 10 Hz to 100 kHz, (ii) a wavelength within the range of 200 nm to 5000 nm, (iii) a pulse energy density within the range of 0.01 J/cm$^2$ to 4 J/cm$^2$ and (iv) a pulse duration of less than 200 ns.

9. The method of claim 1, wherein said high repetition rate laser beam has (i) a pulse frequency within the range of 10 Hz to 100 kHz, (ii) a wavelength within the range of 200 nm to 5000 nm, (iii) a pulse energy within the range of 0.01 J/cm$^2$ to 4 J/cm$^2$ and (iv) a sinusoidal pulse waveform.

10. The method of claim 1, wherein said high repetition rate laser beam has (i) a pulse frequency within the range of 10 Hz to 100 kHz, (ii) a wavelength within the range of 200 nm to 5000 nm, (iii) a pulse energy density within the range of 0.01 J/cm$^2$ to 4 J/cm$^2$ and (iv) a pulse duration that is less than 1 $\mu$s.

* * * * *